(12) United States Patent
Moberg et al.

(10) Patent No.: US 7,714,105 B2
(45) Date of Patent: May 11, 2010

(54) USE OF FRAGMENTS OF OXYTOCIN FOR THE PREPARATION OF A PHARMACEUTICAL COMPOSITION IN ORDER TO CREATE EUSTASIS

(76) Inventors: Kerstin Uvnäs Moberg, Sveavagen 9D, S-182 62 Djursholm (SE); Thomas Lundeberg, Hojdstigen 7, SE-181 31 Lidingö (SE); Maria Petersson, Frestavagen 46, 192 48 Sollentuna (SE)

( * ) Notice: Subject to any disclaimer, the term of this patent is extended or adjusted under 35 U.S.C. 154(b) by 213 days.

(21) Appl. No.: 10/481,623

(22) PCT Filed: Jun. 19, 2002

(86) PCT No.: PCT/SE02/01207

§ 371 (c)(1),
(2), (4) Date: Jul. 12, 2004

(87) PCT Pub. No.: WO02/102832

PCT Pub. Date: Dec. 27, 2002

(65) Prior Publication Data

US 2004/0259805 A1    Dec. 23, 2004

(30) Foreign Application Priority Data

Jun. 19, 2001    (SE)    .................................... 0102184

(51) Int. Cl.
*A61K 38/06*    (2006.01)
*A61K 38/00*    (2006.01)
(52) U.S. Cl. ........................................ 530/331; 514/18
(58) Field of Classification Search .................... 514/16, 514/9, 11, 18
See application file for complete search history.

(56) References Cited

U.S. PATENT DOCUMENTS 4,271,068 A * 6/1981 Kamber et al. .............. 530/336

5,767,083 A * 6/1998 Abajian et al. ................ 514/16

FOREIGN PATENT DOCUMENTS

| EP | 0146113 A2 | 6/1985 |
| WO | WO 00/18425 | 4/2000 |
| WO | WO 0018425 * | 4/2000 |

OTHER PUBLICATIONS

Celis, M.E., et al. 1971 PNAS 68(7): 1428-1433.*
El-Maghraby, M.A. 1976 Journal of the Indian Chemical Society 53(7): 670-672.*
Ivanov, A.K., et al. 1992 Chemistry of Natural Compounds 28(3-4): 344-349.*
Kreil, G. 1984 Methods of Enzymology 106: 218-223.*
Evre, J.C.L., et al. 1995 Chemical Research in Toxicology 8: 414-421.*
Gillessen, D., et al. 1981 Dev Endocrinol 13 Neurohypophyseal Peptide Hormones and Other Biologically Active Peptides: p. 37-47.*
Overweg et al., "Inhibition of the action of oxytocin on the rat uterus by acyclic oxytocin intermediates", The Journal of Pharmacology and Experimental Therapeutics, vol. 161, No. 2, 1968, pp. 342-347.
Khelifa, N. et al., "Cleavage of L-leucine-containing dipeptides by *Clostridium butyricuml*", *Bioorganic & Medicinal Chemistry Letters*, 9, (1999) pp. 109-112.
Murby, M. et al., "Differential degradation of a recombinant albumin-binding receptor in *Escherichia coli*", *Eur. J. Biochem*, 199, 41-46 (1991).
Walter, R. et al., "Neurohypophyseal hormones, analogs, and fragments: Their effect on puromycin-induced amnesia", *Proc. Nat. Acad. Sci*, USA, vol. 72, No. 10, pp. 4180-4184, Oct. 1975.

* cited by examiner

*Primary Examiner*—Maryam Monshipouri
*Assistant Examiner*—Marsha M Tsay
(74) *Attorney, Agent, or Firm*—Young & Thompson

(57) ABSTRACT

The present invention relates to the use di-, tri- and tetrapeptide fragments of oxytocin or mesotocin for the preparation of a pharmaceutical composition in order to create eustasis. The invention also relates to di-, tri- and tetrapeptide fragments of oxytocin or mesotocin for medical use, as well as a pharmaceutical composition comprising at least one di-, tri- or tetrapeptide fragment of oxytocin or mesotocin in order to create eustasis.

8 Claims, No Drawings

SEQUENCE LISTING

<160> NUMBER OF SEQ ID NOS: 19

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: AMIDATION
<220> FEATURE:
<221> NAME/KEY: DISULFID
<222> LOCATION: (1)..(6)

<400> SEQUENCE: 1

Cys Tyr Ile Gln Asn Cys Pro Leu Gly
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: AMIDATION
<220> FEATURE:
<221> NAME/KEY: DISULFID
<222> LOCATION: (1)..(6)

<400> SEQUENCE: 2

Cys Tyr Ile Gln Asn Cys Pro Ile Gly
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Cys or nothing
<220> FEATURE:
<221> NAME/KEY: MISC_FEATURE
<222> LOCATION: (2)..(2)
<223> OTHER INFORMATION: Pro or nothing
<220> FEATURE:
<221> NAME/KEY: MISC_FEATURE
<222> LOCATION: (3)..(3)
<223> OTHER INFORMATION: Leu or Ile
<220> FEATURE:
<221> NAME/KEY: MISC_FEATURE
<222> LOCATION: (4)..(4)
<223> OTHER INFORMATION: Gly or nothing
<220> FEATURE:
<223> OTHER INFORMATION: see specification as filed for detailed
      description of substitutions and preferred embodiments

<400> SEQUENCE: 3

Xaa Xaa Xaa Xaa
1

<210> SEQ ID NO 4
<211> LENGTH: 4

```
<212> TYPE: PRT
<213> ORGANISM: Artificial Sequence
<220> FEATURE:
<223> OTHER INFORMATION: Synthetic peptide

<400> SEQUENCE: 4

Cys Pro Leu Gly
1

<210> SEQ ID NO 5
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: AMIDATION

<400> SEQUENCE: 5

Cys Pro Leu Gly
1

<210> SEQ ID NO 6
<211> LENGTH: 4
<212> TYPE: PRT
<213> ORGANISM: Artificial Sequence
<220> FEATURE:
<223> OTHER INFORMATION: Synthetic peptide

<400> SEQUENCE: 6

Cys Pro Ile Gly
1

<210> SEQ ID NO 7
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: AMIDATION

<400> SEQUENCE: 7

Cys Pro Ile Gly
1

<210> SEQ ID NO 8
<211> LENGTH: 3
<212> TYPE: PRT
<213> ORGANISM: Artificial Sequence
<220> FEATURE:
<223> OTHER INFORMATION: Synthetic peptide

<400> SEQUENCE: 8

Pro Leu Gly
1

<210> SEQ ID NO 9
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
```

```
<222> LOCATION: (3)..(3)
<223> OTHER INFORMATION: AMIDATION

<400> SEQUENCE: 9

Pro Leu Gly
1

<210> SEQ ID NO 10
<211> LENGTH: 3
<212> TYPE: PRT
<213> ORGANISM: Artificial Sequence
<220> FEATURE:
<223> OTHER INFORMATION: Synthetic peptide

<400> SEQUENCE: 10

Pro Ile Gly
1

<210> SEQ ID NO 11
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: AMIDATION

<400> SEQUENCE: 11

Pro Ile Gly
1

<210> SEQ ID NO 12
<211> LENGTH: 3
<212> TYPE: PRT
<213> ORGANISM: Artificial Sequence
<220> FEATURE:
<223> OTHER INFORMATION: Synthetic peptide

<400> SEQUENCE: 12

Cys Pro Leu
1

<210> SEQ ID NO 13
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: AMIDATION

<400> SEQUENCE: 13

Cys Pro Leu
1

<210> SEQ ID NO 14
<211> LENGTH: 3
<212> TYPE: PRT
<213> ORGANISM: Artificial Sequence
<220> FEATURE:
<223> OTHER INFORMATION: Synthetic peptide

<400> SEQUENCE: 14

Cys Pro Ile
```

```
<210> SEQ ID NO 15
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: AMIDATION

<400> SEQUENCE: 15

Cys Pro Ile
1

<210> SEQ ID NO 16
<211> LENGTH: 2
<212> TYPE: PRT
<213> ORGANISM: Artificial Sequence
<220> FEATURE:
<223> OTHER INFORMATION: Synthetic peptide

<400> SEQUENCE: 16

Leu Gly
1

<210> SEQ ID NO 17
<211> LENGTH: 2
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: AMIDATION

<400> SEQUENCE: 17

Leu Gly
1

<210> SEQ ID NO 18
<211> LENGTH: 2
<212> TYPE: PRT
<213> ORGANISM: Artificial Sequence
<220> FEATURE:
<223> OTHER INFORMATION: Synthetic peptide

<400> SEQUENCE: 18

Ile Gly
1

<210> SEQ ID NO 19
<211> LENGTH: 2
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: AMIDATION

<400> SEQUENCE: 19

Ile Gly
1
```

USE OF FRAGMENTS OF OXYTOCIN FOR THE PREPARATION OF A PHARMACEUTICAL COMPOSITION IN ORDER TO CREATE EUSTASIS

The present invention relates to the use di-, tri- and tetrapeptide fragments of oxytocin or mesotocin for the preparation of a pharmaceutical composition in order to create eustasis. The invention also relates to di-, tri- and tetrapeptide fragments of oxytocin or mesotocin for medical use, as well as a pharmaceutical composition comprising at least one di-, tri- or tetrapeptide fragment of oxytocin or mesotocin in order to create eustasis.

BACKGROUND OF THE INVENTION

Oxytocin was one of the first peptide hormones to be isolated and sequenced. It is a nonapeptide with two cysteine residues that form a disulfide bridge between positions 1 and 6 and corresponds to the formula

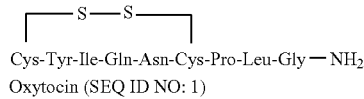

Cys-Tyr-Ile-Gln-Asn-Cys-Pro-Leu-Gly—$NH_2$
Oxytocin (SEQ ID NO: 1)

A similar nonapetide is mesotocin having the formula

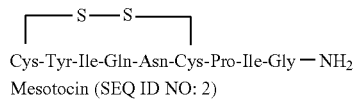

Cys-Tyr-Ile-Gln-Asn-Cys-Pro-Ile-Gly—$NH_2$
Mesotocin (SEQ ID NO: 2)

For a long time the only effects attributed to oxytocin were its stimulating effects on milk ejection and uterine contractions, but in the past decades it has been shown that oxytocin exerts a wide spectrum of effects within the central nervous system, CNS. It has been suggested that oxytocin participates in the control of memory and learning processes and of various types of behaviour such as feeding, locomotion, as well as maternal and sexual behavior. Oxytocin is also suggested to participate in the control of cardiovascular functions, thermoregulation, and pain threshold and fluid balance. There is also evidence that oxytocin is involved in the control of various immunological processes. It has recently been demonstrated that oxytocin injections cause a lowering of blood pressure and increased weight gain—long lasting effects after repetitive administration. As a central stimulating substance oxytocin plays an important role in the interaction between mother and progeny in mammals. The products may also be used prophylactic in young human beings e.g. already in new born babies or young children to prevent the development of diseases later on in life which diseases are dependent on stress conditions during the fetal life. Such conditions may be heart/vessel diseases such as stroke, heart infarct, hypertension, and diabetes.

In the human body oxytocin is produced in the paraventricular nucleus, PVN, and the supraoptic nucleus, SON, of the hypothalamus. It differs by only two amino acids from vasopressin, which is also produced in these nuclei. The magnocellular oxytocinergic neurones of the SON and PVN send oxons to the posterior pituitary from which oxytocin is released into the circulation. Parvocellular neurones that originate in the PVN project into multiple areas within CNS. The oxytocin-producing cells are innervated by cholinergic, catecholaminergic as well as peptidergic neurones. The presence of oxytocin in different tissues outside the brain, such as the uterus, ovaries, testis, thymus, adrenal medulla and pancreas has been demonstrated and oxytocin is suggested to exert local effects in these organs.

A parallel secretion of oxytocin into the brain regions and into the circulation occurs in response to some stimuli such as suckling, but other stimuli can cause separate activation of oxytocinergic neurones, terminating in the brain or the pituitary.

Mesotocin, which has been isolated from frogs, has similar effects as oxytocin.

The oxytocin and mesotocin molecule may be digested into smaller fragments. Of special interest are fragments containing 2-4 peptides obtained by cleavage amino acids from the amino terminal and/or the carboxyl terminal. As used in the context of the present invention, the term "di-, tri- and tetrapeptide fragments of oxytocin or mesotocin" correspond to such fragments. Such fragments may either be amidated or not at the C-terminal. It has now been shown that di-, tri- and tetrapeptide fragments of oxytocin or mesotocin may be used in order to create eustasis.

By the expression "eustasis" we understand a psycho-physiological state, i e a combination of a psychological and physiological state. The psychological state is characterised by calm and positive social interactions such as trust and breast-feeding. The physiological state is characterised by muscle relaxation, lowered cardiovascular activity and enhanced gastrointestinal activity. Besides, pulse rate and blood pressure are kept at a low, healthy and balanced level, and the vagally controlled gastrointestinal tract is activated, promoting digestion and storage of nutrients.

Eustasis should not be confused with euphoria, which is more an intense feeling of joy and reward. Furthermore, the creation of eustasis should not be confused with the treatment of depression or any other disease states. For example, the treatment of depression refers to a conversion from a disease state to a healthy state, whereas the creation of eustasis refers to a conversion from one healthy state to another healthy state.

In the Examples, some compounds according to the invention are administered to rats. A decrease in locomotor activity, blood pressure and hormone levels was noticed, suggested that the compounds have a eustasis creating effect.

U.S. Pat. No. 5,767,083 (D1) discloses the use of Pro-Leu-Gly-$NH_2$ (SEQ ID NO: 8) and Pro-Ile-Gly-$NH_2$ (SEQ ID NO: 9). The first-mentioned oligopeptide is called melanocyte stimulating inhibitory factor, abbreviated MIF, and is used against depression. Furthermore, D1 describes the combination of such oligopeptides known antidepressants such as amitriptyline, fluoxetine, and sertraline.

EP 146 113 (D2) discloses that Pro-Leu-Gly-$NH_2$ (SEQ ID NO: 9) may be used against disease states caused by elevated melanotropine levels, such as high blood pressure. D2 also discloses the dipeptide Leu-Gly-$NH_2$ (SEQ ID NO: 17).

Regulatory Peptides From Molecular Biology to Function, Advances in Biochemical Psychopharmacology, Vol. 33, Ed. E. Costa and M. Trabucchi, Raven Press, New York (1982) (D3) discloses the effect of Leu-Gly-$NH_2$ (SEQ ID NO: 17), acetic acid salt in the treatment of neuropsychiatric illness.

No documents disclose tetrapeptide fragments of oxytocin and mesotocin. As mentioned above, some di- and tripeptide fragments of oxytocin and mesotocin are previously known in the art. However, it is not previously known to use di- and tripeptide fragments of oxytocin and mesotocin in order to create eustasis. Besides, no pharmaceutical compositions comprising the di- and tripeptides and oxytocin or mesotocin are known in the art.

SUMMARY OF THE INVENTION

The present invention relates to the use of di, tri- and tetrapeptide fragments of oxytocin or mesotocin for the preparation of a pharmaceutical composition in order to create eustasis. The invention also relates to di-, tri- and tetrapeptide fragments of oxytocin or mesotocin, preferably for medical use. It also relates to as a pharmaceutical composition comprising at least one di-, tri- or tetrapeptide fragment of oxytocin or mesotocin, and a pharmaceutically acceptable carrier and, optionally oxytocin or mesotocin. Such a pharmaceutical composition may be used in order to create eustasis.

DETAILED DESCRIPTION OF THE INVENTION

One object of the present invention is the use of a compound of the formula (I):

$X_1$-$X_2$-$X_3$-$X_4$       (SEQ ID NO: 3)

wherein $X_1$ is selected from Cys and nothing,
$X_2$ is selected from Pro and nothing;
$X_3$ is selected from Leu and Ile;
$X_4$ is selected from Gly and nothing;
provided that if $X_1$ is Cys, then $X_2$ is Pro;
provided that if $X_4$ is nothing, then $X_1$ is Cys and $X_2$ is Pro;
as well as amidated forms thereof;

for the preparation of a pharmaceutical composition, optionally comprising oxytocin or mesotocin, in order to create eustasis.

By "nothing" is meant that the letters respectively may have no meaning or may represent a bond and that there may be a direct bond between the items (letter, atom or group) situated to the right and to the left, respectively, of the letter designating "nothing". For example, in formula (I), when $X_1$ designates nothing, the resulting molecule corresponds to $X_2$-$X_3$-Gly. When $X_4$ designates nothing, the resulting molecule corresponds to $X_1$-$X_2$-$X_3$.

By "amidated" form is meant that the carboxylic acid group of the carboxyl terminal amino acid residue of the resulting peptide is amidated.

It is preferred that the compound of formula (I) is selected from:

| | |
|---|---|
| Cys-Pro-Leu-Gly | (SEQ ID NO: 4) |
| Cys-Pro-Leu-Gly-NH$_2$, | (SEQ ID NO: 5) |
| Cys-Pro-Ile-Gly, | (SEQ ID NO: 6) |
| Cys-Pro-Ile-Gly-NH$_2$, | (SEQ ID NO: 7) |
| Pro-Leu-Gly, | (SEQ ID NO: 8) |
| Pro-Leu-Gly-NH$_2$, | (SEQ ID NO: 9) |
| Pro-Ile-Gly, | (SEQ ID NO: 10) |
| Pro-Ile-Gly-NH$_2$, | (SEQ ID NO: 11) |
| Cys-Pro-Leu, | (SEQ ID NO: 12) |
| Cys-Pro-Leu-NH$_2$ | (SEQ ID NO: 13) |
| Cys-Pro-Ile, | (SEQ ID NO: 14) |
| Cys-Pro-Ile-NH$_2$ | (SEQ ID NO: 15) |
| Leu-Gly, | (SEQ ID NO: 16) |
| Leu-Gly-NH$_2$, | (SEQ ID NO: 17) |
| Ile-Gly and | (SEQ ID NO: 18) |
| Ile-Gly-NH$_2$. | (SEQ ID NO: 19) |

It is also preferred that the compound is administered in an amount of 1 μg to 1 mg/kg body weight of the patient.

Another object of the present invention is a compound of the formula (I):

$X_1$-$X_2$-$X_3$-$X_4$       (SEQ ID NO: 3)

wherein $X_1$ is selected from Cys and nothing,
$X_2$ is selected from Pro and nothing;
$X_3$ is selected from Leu and Ile;
$X_4$ is selected from Gly and nothing;
provided that if $X_1$ is Cys, then $X_2$ is Pro;
provided that if $X_4$ is nothing, then $X_1$ is Cys and $X_2$ is Pro;
as well as amidated forms thereof;
provided that if $X_1$ is nothing, $X_2$ is Pro, then $X_4$ is Gly in non-amidated form; and
provided that if $X_1$ and $X_2$ are nothing, and $X_3$ is Leu, then $X_4$ is Gly in non-amidated form.

By "non-amidated" form is meant that the carboxylic acid group of the carboxyl terminal amino acid residue of the resulting peptide is not amidated.

It is preferred that the compound of formula (I) is selected from:

| | |
|---|---|
| Cys-Pro-Leu-Gly | (SEQ ID NO: 4) |
| Cys-Pro-Leu-Gly-NH$_2$, | (SEQ ID NO: 5) |
| Cys-Pro-Ile-Gly, | (SEQ ID NO: 6) |
| Cys-Pro-Ile-Gly-NH$_2$, | (SEQ ID NO: 7) |
| Pro-Leu-Gly, | (SEQ ID NO: 8) |
| Pro-Ile-Gly, | (SEQ ID NO: 10) |
| Cys-Pro-Leu, | (SEQ ID NO: 12) |
| Cys-Pro-Leu-NH$_2$ | (SEQ ID NO: 13) |
| Cys-Pro-Ile, | (SEQ ID NO: 14) |
| Cys-Pro-Ile-NH$_2$ | (SEQ ID NO: 15) |
| Leu-Gly, | (SEQ ID NO: 16) |
| Ile-Gly and | (SEQ ID NO: 18) |
| Ile-Gly-NH$_2$. | (SEQ ID NO: 19) |

Another object of the present invention is a compound as defined above for medical use.

Another object of the present invention is a pharmaceutical composition comprising at least one compound as defined above, and a pharmaceutically acceptable carrier and, optionally, oxytocin or mesotocin, in order to create eustasis.

It is preferred that the effective concentration of the compound in the pharmaceutical composition is 4-70% by weight, preferably 0.1-50% by weight.

The invention also relates to the peptides mentioned above in both D- and L-form. Especially the invention relates to the L-form. By inversion of the peptide sequence thereof, the D-form could be converted to the L-form. The effect of the D- and L-forms are the same. These and the peptides above can be produced by methods known to a person skilled in the art e.g. according to Merrifield, P. B., "Solid Phase Synthesis", *Angew. Chemie*, 1985, No. 97, p. 801.

The pharmaceutical compositions are prepared in a manner known to a person skilled in the pharmaceutical art. The carrier or the excipient could be a solid, semi-solid or liquid material that could serve as a vehicle or medium for the active ingredient. Suitable carriers or excipients are known in the art. The pharmaceutical composition could be adapted to oral, parenteral, intravaginal, or topical use and could be administered to the patient as tablets, capsules, suppositories, solutions, suspensions or the like.

The pharmaceutical compositions could be administered orally, e.g. with an inert diluent or with an edible carrier. They could be enclosed in gelatine capsules or be compressed to tablets. For oral therapeutic administration the compounds according to the invention could be incorporated with excipients and used as tablets, lozenges, capsules, elixirs, suspensions, syrups, wafers, chewing gums and the like. These preparations should contain at least 4% by weight of the compounds according to the invention, the active ingredient, but could be varied according to the special form and could, suitably, be 4-70% by weight of the unit. The amount of the active ingredient that is contained in compositions is so high that a unit dosage form suitable for administration is obtained.

The tablets, pills, capsules, lozenges and the like could also contain at least one of the following adjuvants: binders such as microcrystalline cellulose, gum tragacanth or gelatine, excipients such as starch or lactose, disintegrating agents such as alginic acid, Primogel, corn starch, and the like, lubricants such as magnesium stearate or Sterotex, glidants such as colloidal silica dioxide, and sweetening agents such as saccharose or saccharin could be added or flavourings such as peppermint, methyl salicylate or orange flavouring. When the unit dosage form is a capsule it could contain in addition to the type above a liquid carrier such as polyethylene glycol or a fatty oil. Other unit dosage forms could contain other different materials that modify the physical form of the unit dosage form, e.g. as coatings. Accordingly, tablets or pills could be coated with sugar, shellac or other enteric coating agents. A syrup could in addition to the active ingredient contain saccharose as a sweetening agent and some preservatives, dyes and flavouring agents. Materials that are used for preparation of these different compositions should be pharmaceutically pure and non-toxic in the amounts used.

For parental administration the compounds according to the invention could be incorporated in a solution or suspension. Parenteral administration refers to the administration not through the alimentary canal but rather by injection through some other route, as subcutaneous, intramuscular, intraorbital, intracapsular, intraspinal, intrasternal, intravenous, intranasal, intrapulmonary, through the urinary tract, through eye drops, rectal or intravaginal (e.g. as a suppository, a vagitorium, a cream or an ointment), through the lactiferous tract in cattle, into an organ such as bone marrow, etc. Bone marrow may also be treated in vitro. These preparations could contain at least 0.1% by weight of an active compound according to the invention but could be varied to be approximately 0.1-50% thereof by weight. The amount of the active ingredient that is contained in such compositions is so high that a suitable dosage is obtained.

The solutions or suspensions could also comprise at least one of the following adjuvants: sterile diluents such as water for injection, saline, fixed oils, polyethylene glycols, glycerol, propylene glycol or other synthetic solvents, antibacterial agents such as benzyl alcohol or methyl paraben, antioxidants such as ascorbic acid or sodium bisulfite, chelating agents such as ethylene diamine tetraacetic acid, buffers such as acetates, citrates or phosphates, and agents for adjustment of the tonicity such as sodium chloride or dextrose. The parenteral preparation could be enclosed in ampoules, disposable syringes or multiple dosage vessels made of glass or plastic.

For topical administration the compounds according to the invention could be incorporated in a solution, suspension, or ointment. These preparations could contain at least 0.1% by weight of an active compound according to the invention but could be varied to be approximately 0.1-50% thereof by weight. The amount of the active ingredient that is contained in such compositions is so high that a suitable dosage is obtained. The administration could be facilitated by applying touch, pressure, massage, heat, warms, or infrared light on the skin, which leads to enhanced skin permeability. Hirvonen, J., Kalia, Y N, and Guy, R H. Transdermal delivery of peptides by iontophoresis, *Nat Biotechnol* 1996 December; 14(13): 1710-1713 describes how to enhance the transport of a drug via the skin using the driving force of an applied electric field. Preferably, iontophoresis is effected at a slightly basic pH.

Other administration forms are inhalation through the lungs, buccal administration via the mouth, enteral administration via the small intestine, and local administration with a release, preferably a slow release, of the active substance e g in the form of a ring. All these administration forms could be effected by means known by a person skilled in the art.

All publications mentioned herein are hereby incorporated by reference. By the expression "comprising" we understand including but not limited to. Thus, other non-mentioned substances, additives or carriers may be present.

The invention will be illuminated by the following Examples, which are only intended to illuminate and not restrict the invention in any way.

EXAMPLES

Materials and Methods

Animals. Eight week-old male Sprague-Dawley rats (280-300 g) were obtained from B&K Universal AB, Sollentuna, Sweden.

Experimental procedure. SEQ ID NO: 5 was dissolved in physiological saline (1 mg/ml) and administered subcutaneously to six rats at a dose of 1 mg/kg for five consecutive days. Six rats received physiological saline only as a control. Two days after the last treatment, the rats were exposed to blood pressure determination with the cuff technique. The locomotor behaviour was studied three days after the end of the treatment. The next day the animals were decapitated and blood was collected.

Statistics. The results are presented as means ±SD. Statistical analysis was performed by means of 2-way ANOVA followed by Bonferroni's test for post hoc comparison. A Students t-test was performed. p-values of 0.05 or less were regarded as statistically significant.

Example 1

Locomotor Activity Observations

The spontaneous motor activity was observed in a square open-field arena (680×680×450 mm), equipped with two rows of photocells (8×8), sensitive to infrared light. Two identical frames of photocells were placed at two levels, 40 and 125 mm above the floor, respectively. The open-field was enclosed in a ventilated, sound-attenuating box with a Perspex top. Measurements were made in the dark and performed between 0.900-16.00 h.

The number of photocell beam interruptions were collected on an IBM-compatible PC computer allowing the registration of locomotor activity (all interruptions of photobeams at the lower level) and rearing (all interruptions of photobeams at the upper level). The data were subject to a square root transformation. For further details on the apparatus and the computer software used, including a schematic drawing of the equipment, see Ericson, E., Samuelsson, J., and Ahlenius, S. (1991). Photocell measurements of rat motor activity: A contribution to sensitivity and variation in behavioral observations. *J Pharmacol Meth* 25, 111-122. Furthermore, the peripheral activity was measured. By peripheral activity is meant that the animals are located in the corners of the arena. When the animals are frightened, they have a higher tendency to be located in the corners ie have a high peripheral activity. On the contrary, when the animals are more calm, they have a higher tendency to be located in the middle of the arena ie have a lower peripheral activity.

Results

The locomotor activity was significantly decreased in rats treated with SEQ ID NO: 5, as well as the amount of rearing. Likewise, the amount of peripheral activity decreased. Together, these data show that the compounds according to the invention induce a calming effect.

Example 2

Plasma Hormone Determinations

Trunk blood was collected in ice-chilled tubes, containing heparin (10 IU/ml) (Pharmacia-Upjohn, Stockholm, Sweden) and aprotinin (500 IU/ml) (Trasylol, Bayer, Germany). The blood samples were centrifuged and plasma was removed and frozen (−20° C.).

Oxytocin

Oxytocin was measured with a specific radioimmunoassay developed in this laboratory (Stock, S., and Uvnäs-Moberg, K. (1988). Increased plasma levels of oxytocin in response to stimulation of the sciatic and vagal nerves and in response to touch and pinch in anaesthetized rats. *Acta Physiol Scand* 132, 29-34.). Plasma samples were purified with reversed-phase chromatography using C18 Waters SEP-PAK cartridges. The antiserum anti-oxytocin (rabbit) for RIA, KA-19 (Euro Diagnostica, Malmö, Sweden) and the tracer $[^{125}I]$-Tyr$^2$-oxytocin (Du Pont Nen Research Products, Boston, Mass.) were used. The cross-reactivity of the antibody was less than 0.01% with vasopressin, somatostatin LH-RH and ACTH. The limit of detection was 2 pmol/l. The intra- and interassay coefficients of variation were 11 and 13%, respectively.

Gastrin

Gastrin was immunoassayed as described by Smedh, U., and Uvnäs-Moberg, K. (1994) Intracerebroventricularly administered corticotropin-releasing factor releases somatostatin through a colinergic, vagal pathway in freely fed rats. *Acta Physiol Scand* 151, 241-247. The gastrin standard (Pensinsula Laboratories), the antiserum No 260 4 (gift fom J F Rehfeld, Rigshospitalet, Copenhagen Denmark) and the tracer $[^{125}I]$-gastrin 8 Euro Diagnostic, Malmö Sweden were used. The reactivity of the antibody had the same potency for gastrin-17 and gastrin-34. The limit of detection of the assay was 6 pmol/l. The intra- and interassay coefficients of variation were 10 and 13%, respectively.

Cholecystokinin (CCK)

CCK was immunoassayed as described by Smedh and Uvnäs Moberg, supra. Plasma samples were purified with reversed-phase chromatography using C18 Waters SEP PAK cartridges. The CCK standard (Peninsula Laboratories) the antiserum OAL 656 (Otsuka Assay Laboratories, Japan) and the tracer $[^{125}I]$-CCK (Du Pont NEN Research Products Boston, Mass.) were used. The antiserum OAL 656 was raised against N-terminal amino acid residue of sulphated CCK 8 and reacted with CCK 8, CCK 39 but not with gastrin and its related peptides. The limit of detection of the assay was 3-6 pmol/l The intra- and interassay coefficients of variation were 10 and 12% respectively.

Results

The animals treated for five consecutive days with SEQ ID NO: 5 had the hormone levels as shown in Table 1.

TABLE 1

Hormone levels of rats treated with SEQ ID NO: 5 compared to control rats.

| Hormone | Hormone levels in hormone treated rats (N = 6) | Hormone levels in control rats (N = 6) | p-value |
| --- | --- | --- | --- |
| Oxytocin | 29.7 ± 7.2 | 53.6 ± 14.3 | 0.004 |
| Gastrin | 85 ± 19.3 | 130 ± 52.6 | 0.09 |
| CCK | 8.4 ± 3.5 | 14.6 ± 7.6 | 0.06 |

These data indicate that the compounds according to the invention significantly lower the oxytocin levels, whereby the cholinergic vagal mechanisms are influenced. This suggest a stimulating influence on digestion and anabolic metabolism.

Example 3

Measurement of Blood Pressure and Heart Rate

Blood pressure and heart rate were measured on conscious animals by placing a cuff (Kent RTBP-002, Somedic Sales, Farsta, Sweden) on the base of the tail. The cuff was connected to a Grass 7P8 sphygmanometer and a Grass 7P8DC amplifier with a printer. The rats were habituated to the entire test procedure for 2-3 weeks before the procedure started.

Results

The blood pressure was significantly decreased in rats treated with SEQ ID NO: 5. The systolic and diastolic blood pressures are given in Table 2.

TABLE 2

Hormone levels of rats treated with SEQ ID NO: 5 compared to control rats.

| Blood pressure | Value in hormone treated rats (N = 6) | Value in control rats (N = 6) | p-value |
| --- | --- | --- | --- |
| Systolic | 116 ± 9.1 | 132.1 ± 9.2 | 0.01 |
| Diastolic | 87.3 ± 18.9 | 104.9 ± 14.8 | 0.01 |

The invention claimed is:

1. A peptide consisting of the amino acids selected from the group consisting of: (SEQ ID NO: 14) and (SEQ ID NO: 15).

2. A method for relaxing muscles, lowering cardiovascular activity, pulse rate, blood pressure, and to enhance gastrointestinal activity in a patient in need of treatment thereof, comprising administering an effective amount of peptide according to claim 1 to said patient.

3. A pharmaceutical composition comprising:
at least one peptide according to claim 1; and
a pharmaceutically acceptable carrier.

4. A pharmaceutical composition comprising a pharmaceutically acceptable carrier, at least one of oxytocin and mesotocin, and
a peptide according to claim 1.

5. The pharmaceutical composition according to claim 3, wherein the peptide is 4-70% by weight of the composition.

6. The pharmaceutical composition according to claim 3, wherein the peptide is 0.1-50% by weight of the composition.

7. The pharmaceutical composition according to claim 4, wherein the peptide is 4-70% by weight of the composition.

8. The pharmaceutical composition according to claim 4, wherein the peptide is 0.1-50% by weight of the composition.

* * * * *